(12) United States Patent
Errico et al.

(10) Patent No.: US 12,396,702 B2
(45) Date of Patent: Aug. 26, 2025

(54) SYSTEMS, METHODS, AND APPARATUSES FOR QUANTITATIVE ASSESSMENT OF ORGAN MOBILITY

(71) Applicant: KONINKLIJKE PHILIPS N.V., Eindhoven (NL)

(72) Inventors: Claudia Errico, Medford, MA (US); Hua Xie, Cambridge, MA (US); Qianxi Li, Cambridge, MA (US); Ramon Quido Erkamp, Swampscott, MA (US); Shiying Wang, Melrose, MA (US); Elizabeth Brunelle, Portsmouth, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 91 days.

(21) Appl. No.: 18/267,818

(22) PCT Filed: Dec. 14, 2021

(86) PCT No.: PCT/EP2021/085579
§ 371 (c)(1),
(2) Date: Jun. 16, 2023

(87) PCT Pub. No.: WO2022/128975
PCT Pub. Date: Jun. 23, 2022

(65) Prior Publication Data
US 2024/0065668 A1    Feb. 29, 2024

Related U.S. Application Data

(60) Provisional application No. 63/126,966, filed on Dec. 17, 2020.

(51) Int. Cl.
*A61B 8/08* (2006.01)
*A61B 8/00* (2006.01)
*G06T 7/246* (2017.01)

(52) U.S. Cl.
CPC ............ *A61B 8/085* (2013.01); *A61B 8/4254* (2013.01); *A61B 8/5223* (2013.01); *G06T 7/246* (2017.01);
(Continued)

(58) Field of Classification Search
None
See application file for complete search history.

(56) References Cited

U.S. PATENT DOCUMENTS

| 5,615,680 A | 4/1997 | Sano |
| 6,443,896 B1 | 9/2002 | Detmer |

(Continued)

FOREIGN PATENT DOCUMENTS

| WO | 2014057427 A1 | 4/2014 |
| WO | 2019053249 A1 | 3/2019 |
| WO | 2019078577 A1 | 4/2019 |

OTHER PUBLICATIONS

International Search Report and Written Opinion for PCT/EP2021/085579; Mailing date: Mar. 22, 2022, 8 pages.
(Continued)

*Primary Examiner* — Jonathan Cwern

(57) ABSTRACT

An ultrasound imaging system may analyze motion of landmarks in a temporal sequence of image frames to determine mobility of one or more landmarks. In some examples, the sequence of image frames may be analyzed by one or more artificial intelligence models to detect landmarks and generate flow fields for the detected landmarks. The flow fields may be analyzed to determine the isotropy of the movement of the landmarks. The isotropy analysis may be used to generate a quantitative mobility index.

15 Claims, 11 Drawing Sheets

(52) U.S. Cl.
CPC ............... *A61B 8/463* (2013.01); *A61B 8/469* (2013.01); *G06T 2200/24* (2013.01); *G06T 2207/10016* (2013.01); *G06T 2207/10132* (2013.01)

(56) References Cited

U.S. PATENT DOCUMENTS

| | | | |
|---|---|---|---|
| 6,530,885 B1 | 3/2003 | Entrekin et al. | |
| 2012/0128223 A1 | 5/2012 | Rivaz et al. | |
| 2016/0171766 A1* | 6/2016 | Grbic .................... | A61B 17/00 345/423 |

OTHER PUBLICATIONS

Young, S. et al., "Sonographic evaluation of deep endometriosis: protocol for a US radiology practice", Abdom Radiol., 2016, vol. 41, pp. 2364-2379.

Rogers, P.A., "Priorities for Endometriosis Research: Recommendations From an International Consensus Workshop", Reproductive Sciences, 2009, vol. 16 No. 4, pp. 335-346.

Adamson, G.D., "Creating Solutions in Endometriosis: Global Collaboration through the World Endometriosis Research Foundation", Journal of Endometriosis, 2010, vol. 2, No. 1, pp. 3-6.

Benacerraf, B.R. et al., "Sonography should be the first imaging examination done to evaluate patients with suspected", J Ultrasound Med, 2012, vol. 31, pp. 651-653.

Asch, E. et al., "Variations in Appearance of Endometriomas", J Ultrasound Med, 2007, vol. 26, pp. 993-1002.

Hsu, W-C, et al., "Visceral sliding technique is useful for detecting abdominal adhesion and preventing laparoscopic surgical complications", Gynecol Obstet Invest., 2006, vol. 62, No. 2, pp. 75-78.

Marasinghe, J.P. et al., "History, pelvic examination findings and mobility of ovaries as a sonographic marker to detect pelvic adhesions with fixed ovaries", J. Obstet. Gynaecol. Res., 2014, vol. 40, No. 3, pp. 785-790.

Hariharan, B. et al., "Simultaneous Detection and Segmentation", ECCV 2014; Lecture Notes in Computer Science, 2014, vol. 8695, pp. 297-312.

Redmon, J., "YOLO9000: Better, Faster, Stronger", IEEE Conference on Computer Vision and Pattern Recognition (CVPR), 2017, pp. 6517-6525.

Liu, W. et al., "SSD: Single Shot MultiBox Detector", arXiv:1512.02325v5, 2016, 17 pages.

Ilg, E., et al., "FlowNet 2.0: Evolution of Optical Flow Estimation with Deep Networks", arXiv:1612.01925v1, 2016, 16 pages.

Dosovitskiy, A. et al., "FlowNet: Learning Optical Flow with Convolutional Networks", IEEE International Conference on Computer Vision (ICCV), 2015, pp. 2758-2766.

Krizhevsky, A. et al., "ImageNet Classification with Deep Convolutional Neural Networks", NIPS 2012, 9 pages.

\* cited by examiner

SYSTEMS, METHODS, AND APPARATUSES FOR QUANTITATIVE ASSESSMENT OF ORGAN MOBILITY

CROSS-REFERENCE TO PRIOR APPLICATIONS

This application is the U.S. National Phase application under 35 U.S.C. § 371 of International Application No. PCT/EP2021/085579, filed on Dec. 14, 2021, which claims the benefit of U.S. Provisional Patent Application No. 63/126,966, filed on Dec. 17, 2020. These applications are hereby incorporated by reference herein.

TECHNICAL FIELD

The present disclosure pertains to imaging systems and methods for assessing organ mobility based on ultrasound imaging. In particular, imaging systems and methods for generating a quantitative assessment of ovarian and pelvic organ mobility.

BACKGROUND

Endometriosis affects 1 in 10 women during their reproductive years (usually between age 15 and 49), which accounts for approximately 176 million women worldwide. The lining on the inside of the uterus is called the endometrium. Endometriosis is a clinical condition where tissue similar to the endometrium is found outside the uterus. This initiates a chronic inflammatory process and the tissue around the uterus starts scarring. This inflammatory process is usually severe during the menstrual cycle when the endometrium thickens to prepare for the implantation of a fertilized egg. If an egg is not fertilized, the endometrium sheds as normal part of the menstrual cycle. However, in some cases, the endometrium does not fully exit the body during menstruation. Instead, it becomes attached to organs surrounding the uterus such as the fallopian tubes, the ovaries, or the large and small intestine (recto-sigmoid in particular as deep infiltrating endometriosis) creating lesions. The lesions are part of the inflammatory process; hence, they also shed and cause a variety of symptoms including extremely painful, period pain (dysmenorrhea), chronic pelvic pain, bowel problems, and infertility. The earlier endometriosis is detected and treated, the better the results. Treatment for endometriosis usually involves medication or surgery, depending on the spread of the lesions and their size. Pain medication is usually an over the counter pain reliever, and often hormone therapy is recommended since it slows the endometrial tissue growth and prevents new implants of endometrial tissue (e.g., hormonal contraceptive). Laparoscopic surgery is usually an option if the lesions are either too big or to remove endometriosis implants before a pregnancy.

The detection of endometriosis is primarily done with transvaginal ultrasound imaging (TVUS). Sonographically, the endometrioma is an ovarian cyst that has homogeneous low echogenicity, with no evidence of blood inside. Functional cysts disappear or become smaller within the different phases of the menstrual cycle, while endometriosis does not shrink without treatment. The standard TVUS guidelines suggest to examine uterus and ovaries for routine exams. However, in the presence of chronic pain, this examination is only part of the procedure. When a patient is referred for in-depth TVUS, pelvic and rectal examination are necessary to rule in and rule out the presence of obliterations, or endometriosis. The most important portion of the examination for these patients is evaluation of the ovarian and uterus mobility, the cul-de-sac, bowel wall, and rectovaginal septum, and the pouch of Douglas. In particular, the investigation of organ mobility has been demonstrated to be a method able to detect bowel adhesion and most importantly to understand the severity of obliteration between the uterus and the ovaries with respect to other organs in presence of endometriosis. Organ mobility (or lack thereof) may be used to evaluate other medical conditions as well, such as detection of adhesions due to scar tissue (e.g., hypertrophic scarring).

SUMMARY

Movement of organs within an image frame and/or cluster displacement of organs may be assessed to provide one or more mobility maps and/or a mobility index (e.g., organ mobility index), which may be quantitative in some examples. The mobility index can be used as an indicator of a clinical disease, for example, endometriosis. However, the mobility index may be used for other medical conditions where movement of organs with respect to each other are indicative of a condition (e.g., adhesions from hypertrophic scarring).

The systems, methods, and apparatuses may implement landmark detection of pelvic organs (e.g., uterus, ovaries, internal iliac vessels) on B-mode images. Artificial Intelligence (AI) (e.g., deep learning, machine learning, etc.) may be used for landmark detection in some examples. In some examples, the B-mode images may be acquired by transvaginal ultrasound (TVUS) images. B-mode frame-to-frame absolute displacement and/or global movement of pelvic landmarks may be evaluated using AI. The systems, methods, and apparatuses may generate two-dimensional (2D) displacement and/or velocity maps. The maps may then be evaluated to determine the isotropy and/or anisotropy of the motion. Based on the evaluation, a mobility map may be generated, which may permit a user to determine which pelvic structures in a field of view are fixed (e.g., adhered to another structure) or mobile. In some examples, the systems, methods, and apparatuses may generate an ovarian mobility index (OMI), which may be based on an amount of fixed tissue compared to amount of mobile tissue in the generated maps.

Optionally, in some examples, the systems, methods, and apparatuses may cluster organ displacements based on the distribution of the velocity vectors of the velocity map. Optionally, in some examples, inertial measurement unit (IMU) data may be extracted to detect push-pull movement as well as probe rotation to determine what time segment of collected data to apply OMI processing on, give user feedback on properly executed probe motion, and/or exclude processing of data with corrupted motion patterns in the image due abrupt/incorrect probe motion.

According to at least one example of the present disclosure, an ultrasound imaging system may be configured to provide quantification of landmark mobility, and the system may include a non-transitory computer readable medium encoded with instructions and configured to store a temporal sequence of image frames, and at least one processor in communication with the non-transitory computer readable medium and configured to execute the instructions, wherein when executed, the instructions cause the at least one processor to determine whether one or more landmarks are present in individual image frames of the sequence of image frames, output bounding boxes indicating locations of the one or more landmarks determined to be present in the individual image frames, output flow fields for the one or more landmarks determined to be present in the individual image frames based, at least in part, on the bounding boxes, generate values of displacement fields based, at least in part, on the flow fields, generate values of velocity vectors indicating direction and magnitude of motion based, at least in part, on the flow fields, calculate a displacement/velocity isotropy values by taking a ratio of a magnitude of spatially averaged displacement fields divided by the velocity vectors/magnitude of displacement fields, and generate at least one of a mobility map or a mobility index based, at least in part, on the displacement/velocity isotropy values.

According to at least one example of the present disclosure, a method for providing quantification of landmark mobility may include receiving a sequence of image frames, determining whether one or more landmarks are present in individual image frames of the sequence of image frames, providing bounding boxes indicating locations of the one or more landmarks determined to be present in the individual image frames, generating flow fields for the one or more landmarks determined to be present in the individual image frames based, at least in part, on the bounding boxes or entire frames of the sequence of image frames, generating values of displacement fields based, at least in part, on the flow fields, generating values of velocity vectors indicating direction and magnitude of motion based, at least in part, on the flow fields, calculating a displacement/velocity isotropy values by taking a ratio of a magnitude of spatially averaged displacement fields divided by the velocity vectors/magnitude of displacement fields, and generating at least one of a mobility map or a mobility index based, at least in part, on the displacement/velocity isotropy values. In some embodiments, the method for providing quantification of landmark mobility is a computer implemented method. In some embodiments, the determining whether the one or more landmarks are present and providing the bounding boxes are performed by a first artificial intelligence (AI) model and wherein generating the flow fields is performed by a second artificial intelligence (AI) model. In an embodiment, the second AI model includes a FlowNet network. In some other embodiments, the method for providing quantification of landmark mobility further comprises: segmenting the mobility map based, at least in part, on the displacement/velocity isotropy values; and generating a mobility mask including one or more regions based, at least in part, on segmentation of the mobility map. In some embodiments, the method for providing quantification of landmark mobility further comprises: clustering the one or more landmarks present in individual image frames of the sequence of image frames based on at least one of relative movement or absolute movement of the one or more landmarks. In some embodiments, the method for providing quantification of landmark mobility further comprises generating at least one of a displacement map based on the values of the displacement fields or a velocity map based on the values of the velocity vectors. In some embodiments, the method further for providing quantification of landmark mobility comprises: receiving probe movement data for an ultrasound probe from an inertial measurement unit; and excluding individual images of the image sequence from the image sequence associated with at least one of abrupt motion of the ultrasound probe or rotational motion of the ultrasound probe. In some embodiments, the mobility index is indicative of a level of a clinical condition.

According to at least one example of the present disclosure, there is a computer program product comprising computer readable medium. The computer readable medium has computer readable code embodied therein, and the computer readable code is configured such that, on execution by a suitable computer or processor, the computer or processor is caused to perform the method of for providing quantification of landmark mobility.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed apparatuses, systems and methods, and it is to be understood that other embodiments may be utilized and that structural and logical changes may be made without departing from the spirit and scope of the present disclosure. Moreover, for the purpose of clarity, detailed descriptions of certain features will not be discussed when they would be apparent to those with skill in the art so as not to obscure the description of the present apparatuses, systems, and methods. The following detailed description is therefore not to be taken in a limiting sense, and the scope of the present system is defined only by the appended claims.

Organ mobility may be an indicator of degree and/or severity of certain medical conditions. For example, ovarian mobility evaluated via TVUS can be used as a "soft marker" to indicate the degree and severity of obliteration in the presence of endometriosis. Fixation of the ovaries and reduced mobility of the fallopian tubes due to pelvic adhesions may be features of pelvic endometriosis.

Usually, a mobility assessment is done during an in-depth ultrasound exam to find out whether pelvic organs are adhering to one another or not. For example, for endometriosis, the ovaries are adhering to other pelvic organs or not. Knowing the degree of obliteration may be necessary before proceeding with a laparoscopy surgery.

Currently, there are no quantitative assessments of organ mobility. For example, in the current clinical practice, fixed or mobile ovaries are qualitatively evaluated by expert sonographers. Ovarian mobility is diagnosed by assessing the ovaries mobility with respect to the uterus and ipsilateral internal iliac vessels. The assessment is done by applying a gentle pressure (push-pull) with the TVUS probe on the ovaries. If the ovaries move freely over the ipsilateral internal iliac vessels or the uterus with the gentle pressure, then they can be considered 'mobile'. The ovaries are instead considered "fixed" when they do not move freely with respect to the uterus and/or ovarian fossa due to the presence of pelvic adhesions. Today this assessment is not done quantitatively, rather it is only supported by a qualitative observation of the flexibility of the pelvic organs during TVUS.

Figure 1:
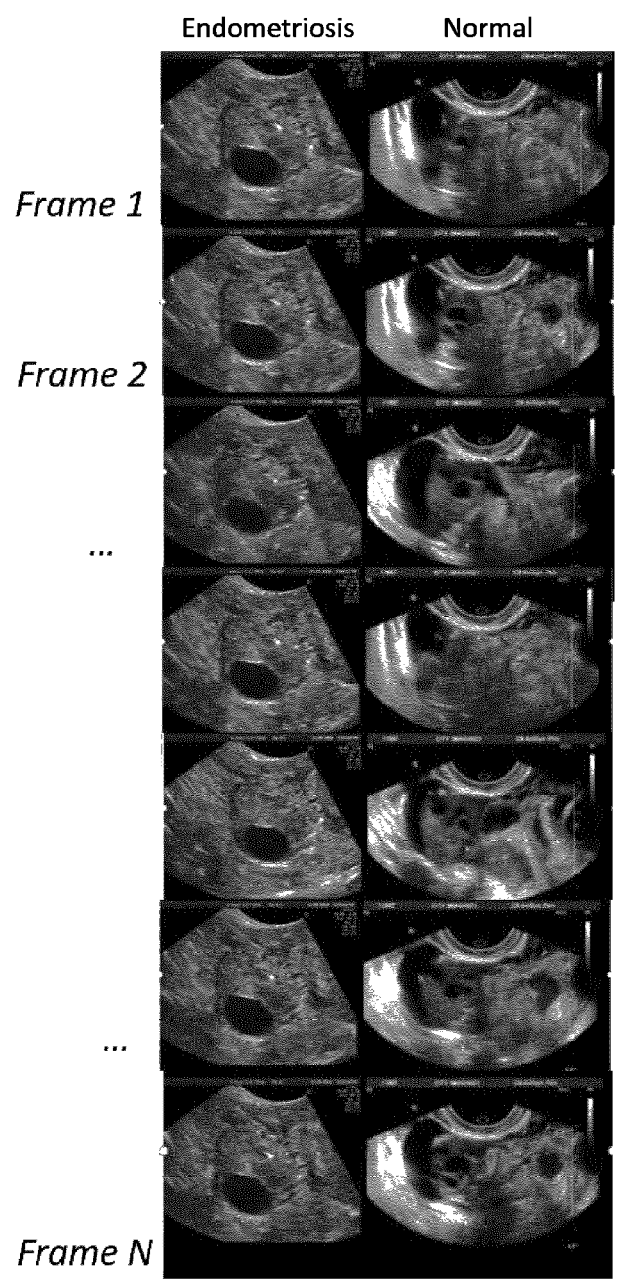
FIG. 1 shows examples of B-mode frame sequences during a push-pull procedure for a case with endometriosis and a normal case.

FIG. 1 shows examples of B-mode frame sequences during a push-pull procedure for a case with endometriosis and a normal case. In the left column there is a serious degree of obliteration, since the cyst is adhering to the adjacent pelvic tissue and the whole structure is very fixed when the sonographer is trying to push the pelvic structures to double check their mobility. On the right column, the same exact push-pull procedure is performed on a healthy uterus where the pelvic organs are very free to move (the features on the image are changing in each frame).

The earlier the detection of endometriosis, the earlier it can be treated. In the current practice, the detection of endometriosis, particularly at early stages, could be missed by non-experienced sonographers. This is a growing concern as the number of trained sonographers is being outpaced by the increasing use of ultrasound in both developed and developing countries. Accordingly, a quantitative measurement of organ mobility, such as ovarian mobility, may be desirable. A quantitative assessment of organ mobility may improve detection and diagnosis of various medical conditions associated with organ mobility, such as the endometriosis.

According to the present disclosure, artificial intelligence (AI) may be used to make an intelligent assessment of organ mobility, such as ovarian mobility, by examining the motion of the organ(s) with respect to adjacent pelvic organs. As used herein, AI refers to machine learning, deep learning, and combinations thereof. The correlation with which the pelvic landmarks in the B-mode ultrasound images are moving, may be translated into an obliteration (e.g., mobility) index. The mobility index may be indicative of a clinical condition (e.g., endometriosis) and/or a severity/level of the clinical condition. The mobility index may be leveraged to cluster pelvic landmarks that move together (e.g., ovaries and uterus move as a single block in presence of deep infiltrating pelvic endometriosis). Additionally or alternatively, the mobility index may be used to generate a mobility mask. The mobility mask may be displayed side-by-side with the B-mode image to the user to indicate the level of obliteration in the field of view during an organ mobility assessment procedure (e.g., applying gentle pressure with the TVUS probe).

Figure 2:
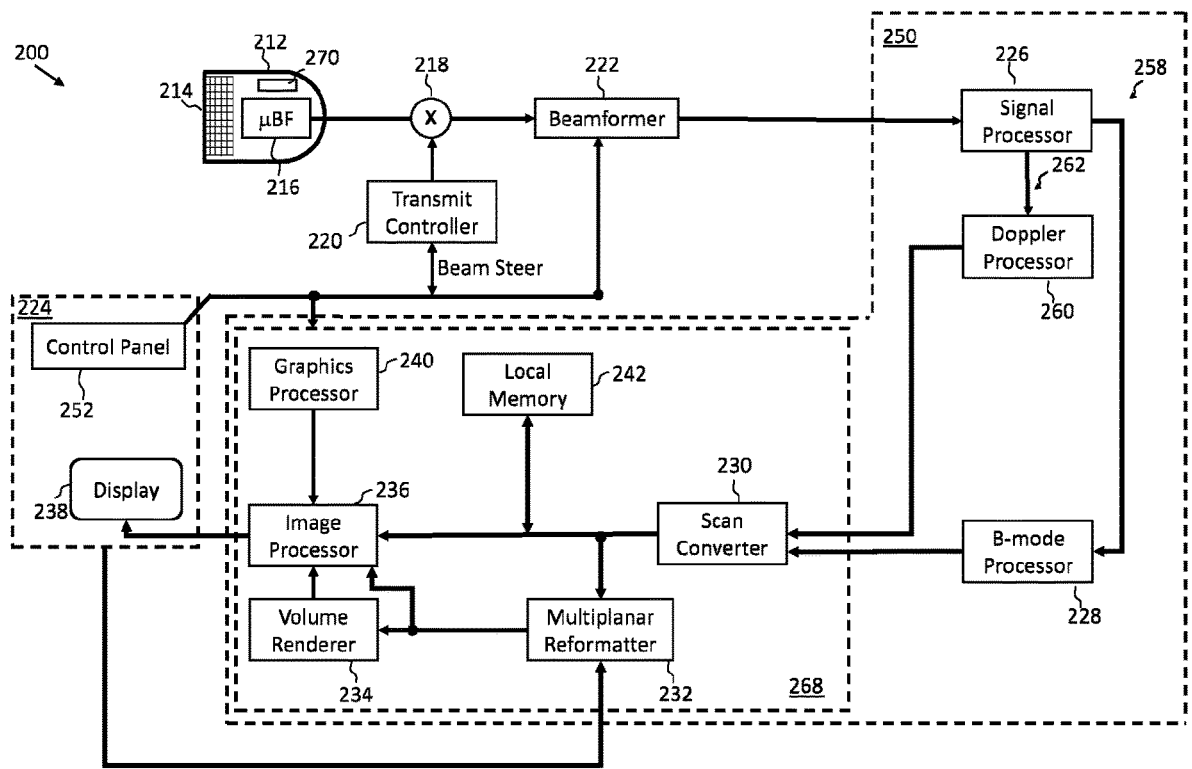
FIG. 2 is a block diagram of an ultrasound system in accordance with principles of the present disclosure.

FIG. 2 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as a transvaginal ultrasound (TVUS) probe. The transducer array 214 is configured to transmit ultrasound signals (e.g., beams, waves) and receive echoes responsive to the ultrasound signals. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

Optionally, in some examples, the ultrasound probe 212 may include a inertial measurement unit (IMU) 270. The IMU 270 may include an accelerometer, a gyroscope, a magnetometer, and/or a combination thereof. The IMU 270 may provide data relating to the velocity, acceleration, rotation, angular rate, and/or orientation of the probe 212 (collectively, probe movement data).

In some embodiments, the transducer array 214 may be coupled to a microbeamformer 116, which may be located in the ultrasound probe 212, and which may control the transmission and reception of signals by the transducer elements in the array 214. In some embodiments, the microbeamformer 216 may control the transmission and reception of signals by active elements in the array 214 (e.g., an active subset of elements of the array that define the active aperture at any given time).

In some embodiments, the microbeamformer 216 may be coupled, e.g., by a probe cable or wirelessly, to a transmit/receive (T/R) switch 218, which switches between transmission and reception and protects the main beamformer 222 from high energy transmit signals. In some embodiments, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface (e.g., processing circuitry 250 and user interface 224).

The transmission of ultrasonic signals from the transducer array 214 under control of the microbeamformer 216 is directed by the transmit controller 220, which may be coupled to the T/R switch 218 and a main beamformer 222. The transmit controller 220 may control the direction in which beams are steered. Beams may be steered straight ahead from (orthogonal to) the transducer array 214, or at different angles for a wider field of view. The transmit controller 220 may also be coupled to a user interface 224 and receive input from the user's operation of a user control. The user interface 224 may include one or more input devices such as a control panel 252, which may include one or more mechanical controls (e.g., buttons, encoders, etc.), touch sensitive controls (e.g., a trackpad, a touchscreen, or the like), and/or other known input devices.

In some embodiments, the partially beamformed signals produced by the microbeamformer 216 may be coupled to a main beamformer 222 where partially beamformed signals from individual patches of transducer elements may be combined into a fully beamformed signal. In some embodiments, microbeamformer 216 is omitted, and the transducer array 214 is under the control of the main beamformer 222 which performs all beamforming of signals. In embodiments with and without the microbeamformer 216, the beamformed signals of the main beamformer 222 are coupled to processing circuitry 250, which may include one or more processors (e.g., a signal processor 226, a B-mode processor 228, a Doppler processor 260, and one or more image generation and processing components 268) configured to produce an ultrasound image from the beamformed signals (e.g., beamformed RF data).

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 258 which couples the signals from the signal processor 226 to a B-mode processor 228 for producing B-mode image data.

The B-mode processor can employ amplitude detection for the imaging of structures in the body. The signals produced by the B-mode processor 228 may be coupled to a scan converter 230 and/or a multiplanar reformatter 232. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format. The multiplanar reformatter 232 can convert echoes which are received from points in a common plane in a volumetric region of the body into an ultrasonic image (e.g., a B-mode image) of that plane, for example as described in U.S. Pat. No. 6,443,896 (Detmer). The scan converter 230 and multiplanar reformatter 232 may be implemented as one or more processors in some embodiments.

A volume renderer 234 may generate an image (also referred to as a projection, render, or rendering) of the 3D dataset as viewed from a given reference point, e.g., as described in U.S. Pat. No. 6,530,885 (Entrekin et al.). The volume renderer 234 may be implemented as one or more processors in some embodiments. The volume renderer 234 may generate a render, such as a positive render or a negative render, by any known or future known technique such as surface rendering and maximum intensity rendering.

In some embodiments, the system may include a Doppler signal path 262 which couples the output from the signal processor 226 to a Doppler processor 260. The Doppler processor 260 may be configured to estimate the Doppler shift and generate Doppler image data. The Doppler image data may include color data which is then overlaid with B-mode (i.e. grayscale) image data for display. The Doppler processor 260 may be configured to filter out unwanted signals (i.e., noise or clutter associated with non-moving tissue), for example using a wall filter. The Doppler processor 260 may be further configured to estimate velocity and power in accordance with known techniques. For example, the Doppler processor may include a Doppler estimator such as an auto-correlator, in which velocity (Doppler frequency, spectral Doppler) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some embodiments, the velocity and/or power estimates may undergo further threshold detection to further reduce noise, as well as segmentation and post-processing such as filling and smoothing. The velocity and/or power estimates may then be mapped to a desired range of display colors in accordance with a color map. The color data, also referred to as Doppler image data, may then be coupled to the scan converter 230, where the Doppler image data may be converted to the desired image format and overlaid on the B-mode image of the tissue structure to form a color Doppler or a power Doppler image. In some examples, the power estimates (e.g., the lag-0 autocorrelation information) may be used to mask or segment flow in the color Doppler (e.g., velocity estimates) before overlaying the color Doppler image onto the B-mode image.

Outputs from the scan converter 230, the multiplanar reformatter 232, and/or the volume renderer 234 may be coupled to an image processor 236 for further enhancement, buffering and temporary storage before being displayed on an image display 238. A graphics processor 240 may generate graphic overlays for display with the images. These graphic overlays can contain, e.g., standard identifying information such as patient name, date and time of the image, imaging parameters, and the like. For these purposes the graphics processor may be configured to receive input from the user interface 224, such as a typed patient name or other annotations. The user interface 224 can also be coupled to the multiplanar reformatter 232 for selection and control of a display of multiple multiplanar reformatted (MPR) images.

The system 200 may include local memory 242. Local memory 242 may be implemented as any suitable non-transitory computer readable medium (e.g., flash drive, disk drive). Local memory 242 may store data generated by the system 200 including ultrasound images, executable instructions, imaging parameters, training data sets, or any other information necessary for the operation of the system 200. In some examples, local memory 242 may include multiple memories, which may be the same or of different type. For example, local memory 242 may include a dynamic random access memory (DRAM) and a flash memory.

As mentioned previously system 200 includes user interface 224. User interface 224 may include display 238 and control panel 252. The display 238 may include a display device implemented using a variety of known display technologies, such as LCD, LED, OLED, or plasma display technology. In some embodiments, display 238 may comprise multiple displays. The control panel 252 may be configured to receive user inputs (e.g., exam type, imaging parameters). The control panel 252 may include one or more hard controls (e.g., buttons, knobs, dials, encoders, mouse, trackball or others). In some embodiments, the control panel 252 may additionally or alternatively include soft controls (e.g., GUI control elements or simply, GUI controls) provided on a touch sensitive display. In some embodiments, display 238 may be a touch sensitive display that includes one or more soft controls of the control panel 252.

In some embodiments, various components shown in FIG. 2 may be combined. For instance, the multiplanar reformatter 232 and volume renderer 234 may be implemented as a single processor. In some embodiments, various components shown in FIG. 2 may be implemented as separate components. For example, signal processor 226 may be implemented as separate signal processors for each imaging mode (e.g., B-mode, Doppler). In another example, the image processor 236 may be implemented as separate processors for different tasks and/or parallel processing of a same task. In some embodiments, one or more of the various processors shown in FIG. 2 may be implemented by general purpose processors and/or microprocessors configured to perform the specified tasks. In some examples, the processors may be configured by providing instructions for the tasks from a non-transitory computer readable medium (e.g., from local memory 242). The instructions may then be executed by the processors. In some embodiments, one or more of the various processors may be implemented as application specific circuits. In some embodiments, one or more of the various processors (e.g., image processor 236) may be implemented with one or more graphical processing units (GPU).

Principles of the present disclosure will be described with reference to ovarian mobility and detection and/or grading of endometriosis. However, this is merely for exemplary purposes, and the principles of the present disclosure may be applied to the mobility of other organs and detection and/or grading of other conditions. For example, principles of the present disclosure may also be applied to mobility of the bladder and/or intestines. Other conditions may include scarring and/or stretched supportive tissue (e.g., fascia, ligaments). In another example, mobility of an implantable device may be evaluated to determine proper placement/ implantation.

During a mobility exam, a user may apply a push-pull motion to the ultrasound probe 212 to apply pressure to one or more organs. For example, during a transvaginal exam, the TVUS probe may be inserted and removed (or partially removed) to apply pressure to the pelvic organs, such as the ovaries. The pressure may cause temporary displacement of the organs. The ultrasound system 200 may acquire a temporal sequence of image frames via the transducer array 214 of the probe 212 during the mobility exam. The image frames may include one or more organs in a field of view of the transducer array 214. For example, in an ovarian mobility exam, one or both ovaries, at least a portion of the uterus, at least a portion of the bowels, and/or at least a portion of the internal iliac vessels may be present in the image frames, or at least some of the image frames.

The sequence of image frames may then be analyzed by one or more processors, such as image processor 236. In some examples, the image processor 236 may include any one or more machine learning, AI algorithms, and/or multiple neural networks (collectively, AI models). In some examples, image processor 236 may include one or more of a deep neural network (DNN), a convolutional neural network (CNN), a recurrent neural network (RNN), an autoencoder neural network and/or single-shot-detector, or the like, to segment and identify organs (e.g., landmark detection) in the image frames, evaluate the frame-to frame displacement and movement of the organs (e.g., movement analysis), and/or generate clusters of organ displacements (e.g., cluster analysis). The AI models may be implemented in hardware (e.g., neurons of a neural network are represented by physical components) and/or software (e.g., neurons and pathways implemented in a software application) components. Neural networks implemented according to the present disclosure may use a variety of topologies and learning algorithms for training the neural networks to produce the desired output. For example, a software-based neural network may be implemented using a processor (e.g., single or multi-core CPU, a single GPU or GPU cluster, or multiple processors arranged for parallel-processing) configured to execute instructions, which may be stored in computer readable medium, and which when executed cause the processor to perform a trained algorithm. In some examples, the image processor 236 may implement AI in combination with other image processing methods (e.g., segmentation, histogram analysis).

In various examples, the AI models may be trained using any of a variety of currently known or later developed learning techniques to obtain a neural network (e.g., a trained algorithm or hardware-based system of nodes) that is configured to analyze input data in the form of ultrasound images, measurements, and/or statistics. In some embodiments, the AI may be statically trained. That is, the AI models may be trained with a data set and deployed on the system 200 and implemented by image processor 236. In some embodiments, the AI models may be dynamically trained. In these examples, the AI models may be trained with an initial data set and deployed on the system 200. However, the AI models may continue to train and be modified based on ultrasound images acquired by the system 200 after deployment of the AI models on the system and implemented by the image processor 236.

In some examples, the output of one or more of the AI models may be used to generate a displacement map, a velocity map, a mobility map, and/or mobility mask. The maps may be used to determine the isotropy and/or anisotropy of the motion/displacement. The determined isotropy and/or anisotropy may be used to generate an organ mobility (e.g., obliteration) index (OMI). In some examples, the maps, determination of isotropy and/or anisotropy, and/or the OMI may be generated by the image processor 236.

Optionally, in some examples, probe movement data from the IMU 270 may be provided to one or more processors, such as the image processor 236, B-mode processor 228, and/or scan converter 230. The probe movement data may be used to determine which image frames of the sequence to provide to the AI for analysis. For example, image frames including data associated with corrupted motion patterns in the image frame due abrupt/incorrect probe motion may be excluded from analysis. Additionally or alternatively, the prove movement data may be used to provide user feedback on proper execution of probe motion for the push-pull technique for the mobility exam.

For a consistent mobility measurement, the probe 212 should apply a significant push to the surrounding tissue, while at the same time, the probe 212 should not rotate. The rotation may cause out of plane motion. Out of plane motion may create inaccuracies in the motion tracking of the AI, for example, due to faster decorrelation rates of the structures being tracked. In addition if organ structures change shape over the elevational dimension, out of plane motion may create a false impression of motion patterns where there is no motion. By differentiating the push-pull movement from the rotation of the probe using the data from the IMU 270 to selectively process data and/or provide feedback to the user about proper execution of the push-pull motion, operator variability when performing the mobility exam may be reduced.

Figure 3:
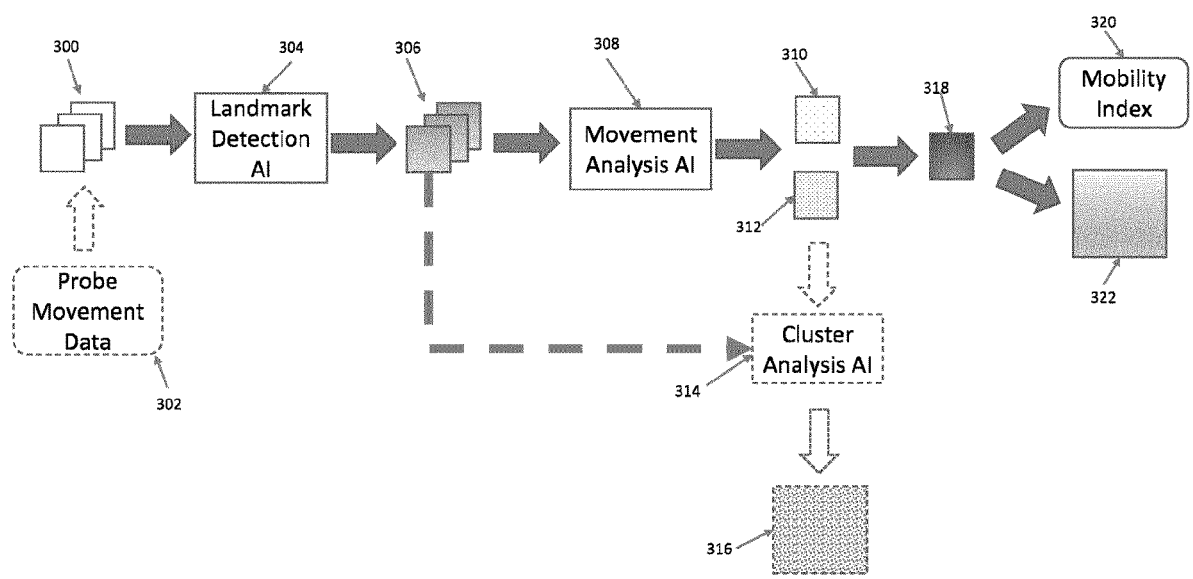
FIG. 3 is a diagram illustrating the inputs and outputs of the artificial intelligence models in accordance with principles of the present disclosure.

FIG. 3 is a diagram illustrating the inputs and outputs of the artificial intelligence models in accordance with principles of the present disclosure. In some examples, the AI models may be implemented by one or more processors included in an ultrasound imaging system, such as ultrasound imaging system 200.

A temporal sequence of image frames 300 acquired during a mobility exam may be provided to a landmark detection and/or organ classification AI model 304 that detects organs and/or other physiological features (e.g., blood vessels), collectively referred to as landmarks, within the sequence of image frames 300. The sequence of image frames 300 may have been acquired by an ultrasound probe, such as ultrasound probe 212. Optionally, in some examples, probe movement data 302 may be used to block/remove individual frames from the sequence of image frames 300 prior to being provided to the landmark detection AI model 304. For example, image frames associated with abrupt and/or incorrect (e.g., rotational) motion may be excluded from the sequence of image frames 300 provided to the landmark detection AI model 304. In some examples, the probe movement data 302 may be provided by an IMU associated with the probe, such as IMU 270.

In some examples, a landmark detection AI model 304 may include multiple deep learning networks where the outputs from one network may be leveraged to initiate the training of a new deep learning network designed to learn a different task, meaning multiple networks can be leveraged to obtain the final output of the landmark detection AI model 304. Simultaneous detection and segmentation (SDS), YOLOv2, MobileNet SSD lite, SSD: Single Shot MultiBox Detector networks are examples of suitable deep learning networks that can be trained to perform landmark detection in the sequence of image frames 300. In some examples, the output 306 of the landmark detection AI model 304 may include a position of one or more predicted bounding boxes (BB) in image coordinates (xo, zo, width of the BB, height of BB), where each BB is associated with a different landmark, for example, the uterus, ovaries, and iliac vessels. In some examples, the output 306 of landmark detection AI model 304 may be sequence of image frames 300 with the bounding boxes tagged, linked, and/or otherwise associated with the appropriate image frames of the sequence of image frames 300. Additionally or alternatively, the landmark detection may be performed by other image segmentation techniques (e.g., edge detection, histogram analysis) to generate the bounding boxes in some examples.

The output 306 from landmark detection AI model 304 may be provided to a movement analysis AI model 308. The sequence of image frames 300 may also be provided to the movement analysis AI model 308 in examples where the output 306 can include the coordinates of bounding boxes, and/or the entire corresponding image frames. The movement analysis AI model 308 may include a deep learning network trained to extract the optical flow—the motion pattern(s) of the landmarks detected by the landmark detection AI model 304. In other words, the movement analysis AI model 308 determines the 2D displacement of organs and/or other physiological features across temporally adjacent image frames. A suitable deep learning network that may be included in the movement analysis model 308 will be described in more detail with reference to FIG. 4. Additionally or alternatively, movement analysis may be performed by other techniques such as speckle analysis.

The output generated by the movement analysis AI model 308 may be used to generate displacement values of displacement fields and values of velocity vectors. These values may be used to generate a displacement map 310 and/or velocity map 312. The displacement map 310 provides a graphical depiction of the displacement fields of the landmarks and the velocity map 312 provides a graphical depiction of the magnitude and direction of movement of individual pixels of individual image frames of the image sequence 300. Example displacement maps are shown and described in reference to FIG. 5A and example velocity maps are shown and described with reference to FIG. 5B.

The displacement and velocity data of the displacement map 310 and the velocity map 312, respectively, may be analyzed to quantify the displacement/velocity isotropy. The degree of isotropy is the ratio of the magnitude of spatially averaged displacement/velocity vectors and magnitude of displacement/velocity vectors. The quantified isotropy values may be used to generate a mobility map 318. Example mobility maps are shown and described in reference to FIG. 6. In some examples, the mobility map 318 may be generated by one or more processors, such as image processor 236.

The isotropy data provided to generate the mobility map 318 may be used to generate a quantitative mobility index (e.g., obliteration index) 320. From the absolute and relative movement of the landmarks (e.g., pelvic structures) determined from the movement analysis AI model 308, along with the bounding boxes for landmark detection from the landmark detection AI model 304, the free and fixed tissue may be determined. For example, for ovarian mobility, if the TVUS B-mode image has a size of 300×300 and the landmarks on the B-mode adjacent images (Frame N and Frame N+1) occupy 75% of the field of view, how much tissue is freely moving or is fixed may be extracted from the displacement correlation. The mobility index 320 may be a percentage of the freely moving tissue compared to the total tissue in some examples. In these examples, a high percentage may indicate high mobility and a low percentage may indicate low mobility. In some applications, the mobility index 320 may be used to detect and/or grade medical conditions. For example, a condition may be determined when the mobility index 320 is equal to or below a threshold value. In another example, a condition may be determined to be a certain grade based on ranges of values of the mobility index 320. In some examples, the mobility index 320 may be generated by one or more processors, such as image processor 236.

The isotropy data provided to generate the mobility map 318 may be used to generate a mobility mask 322. The mobility mask 322 may be a user-friendly depiction of the data from the mobility map 318 that is overlaid on at least one of the images of the sequence of image frames 300. The mobility mask 322 may delineate different regions by outlines, colors, and/or shades based on the mobility data from the mobility map 318. Example mobility masks are shown and described in reference to FIG. 7. In some examples, the mobility mask 322 may be generated by one or more processors, such as image processor 236.

Figure 8:
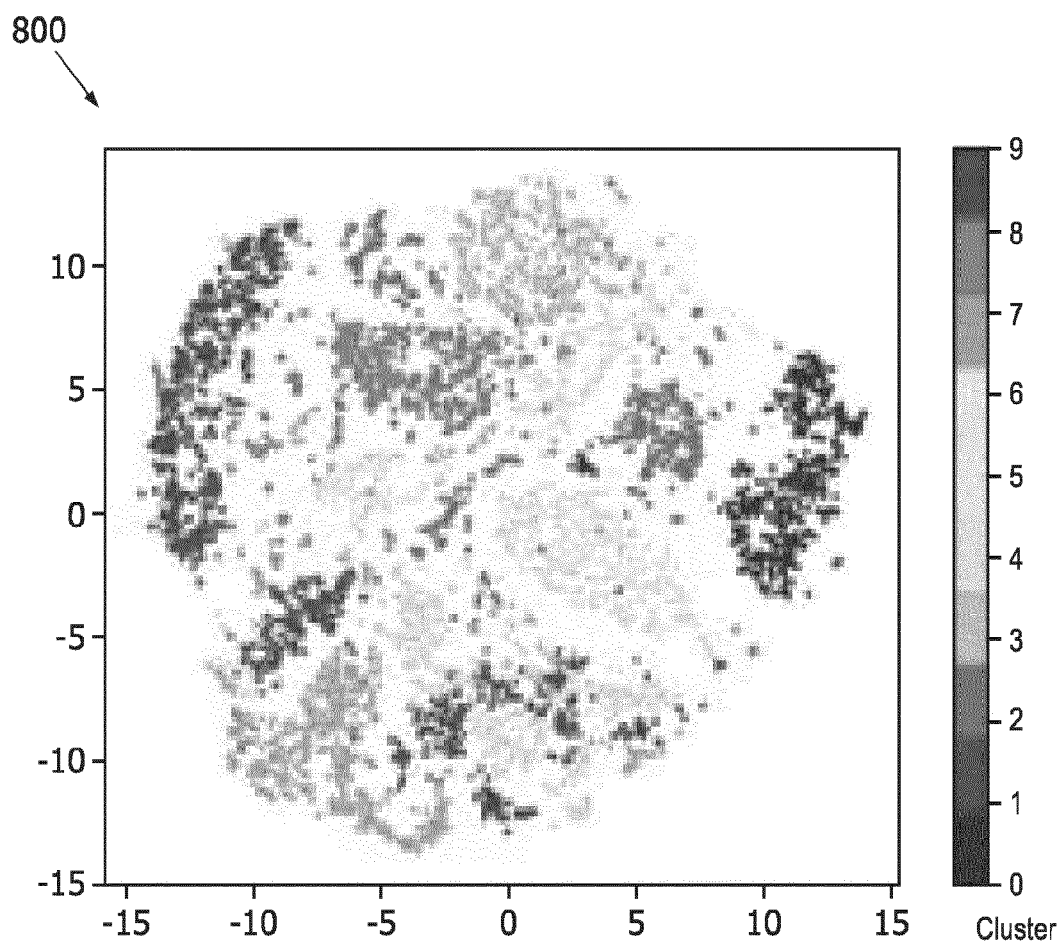
FIG. 8 is an example cluster map of pelvic organs according to principles of the present disclosure.

Optionally, the output of the movement analysis AI model 308 and the output of the landmark detection AI model 304 may be provided to a cluster analysis AI model 314. The image frames 300 may also be provided to the cluster analysis AI model 314 when the output 306 does not include the image frames 300. The cluster analysis AI model 314 may analyze the spatial coherence with which velocity vectors move across temporally adjacent frames of the sequence of image frames 300. The cluster analysis AI model 314 may be trained to cluster the landmarks according to their absolute and relative movement. In some examples, the cluster analysis AI model 314 includes a deep learning model to determine how many unique groups are included in a distribution of trajectories. The model may use a G-means clustering algorithm which may discover the number of clusters automatically using a statistical test in some examples. Other algorithms and/or models may be used in other examples. Trajectory clustering may be used to fade the movements at the boundaries of pelvic landmarks in some examples. The cluster analysis AI model 314 may output a cluster map 316. An example cluster map of pelvic organs is shown in FIG. 8.

In some examples, all of the AI models shown in FIG. 3 may be implemented by different processors. In some examples, one or more of the AI models shown in FIG. 3 may be implemented by a same processor. In some examples, one or more of the AI models may be implemented by multiple processors. In some examples, the mobility map 318, mobility index 320, and/or mobility mask 322 may be generated by the same or different processor(s) as the at least one processor used to implement the AI models.

Figure 4:
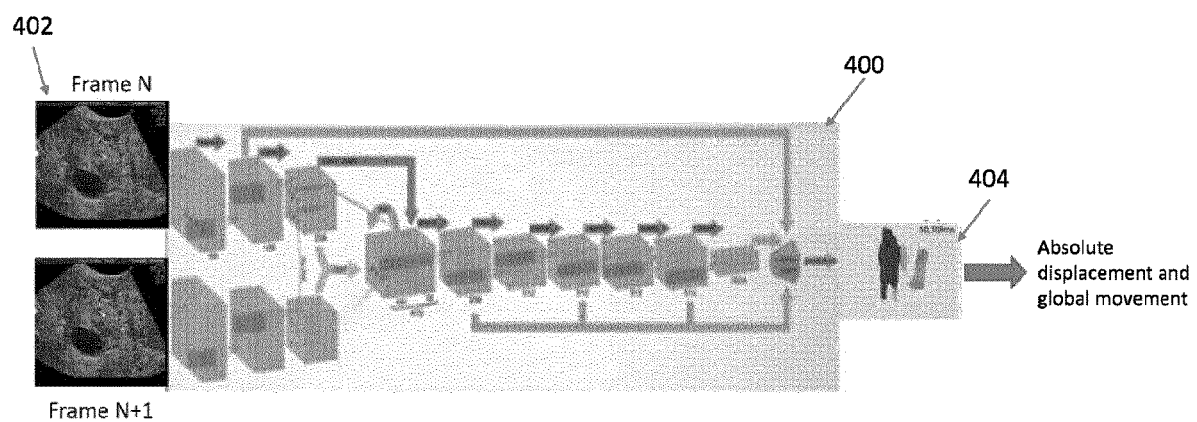
FIG. 4 is a diagram illustrating a neural network suitable for implementing an artificial intelligence model in accordance with principles of the present disclosure.

FIG. 4 is a diagram illustrating a neural network suitable for implementing an artificial intelligence model in accordance with principles of the present disclosure. In some examples, the movement analysis AI model 308 may include one or more convolutional neural networks. In some examples, one or more of the convolutional neural networks may be a FlowNet network 400. FlowNets are convolutional neural networks designed to learn the correlation between adjacent frames, and rely on the displacement of objects (e.g., landmarks) across frames. The input to the FlowNet network 400 may be consecutive image frames 402 (e.g., temporal sequence of image frames 300) and object location information (e.g., output 306 from the landmark detection AI model 304). The FlowNet network 400 may output predicted flow fields 404 for the objects within the image frames 402. Flow fields 404 may also be referred to interchangeably as displacement fields. The flow fields 404 may permit analysis of absolute motion and/or global movement related to the objects within the frames 402. In some examples, the flow fields 404 may be used to generate displacement and/or velocity maps, such as displacement map 310 and velocity map 312, respectively.

In the example FlowNet network 400 shown in FIG. 4, consecutive image frames are input into separate identical processing streams. The processing streams include one or more convolutional layers. After passing through the separate processing streams, the image frames are combined by a correlation layer that compares the feature maps output by the last convolutional layers of the processing streams. The combined image frames are passed through one or more convolutional layers to generate the predicted flow fields 404. Optionally, the output may pass through a variational refinement layer to generate the predicted flow fields 404. Additional details and alternative structures for FlowNet network 400 may be found in A. Dosovitskiy et al., "FlowNet: Learning Optical Flow with Convolutional Networks," 2015 *IEEE International Conference on Computer Vision (ICCV)*, Santiago, 2015, pp. 2758-2766.

The flow fields 404 may be generated with FlowNet network 400 as shown in FIG. 4. Alternatively, other methods such as speckle tracking may be used to identify the motion of the landmarks in the image frames 402. In some examples, ground truth generation for flow patterns can be obtained by generating flow maps with conventional frame-to-frame tracking methods such as speckle tracking for training the FlowNet network 400.

Figures 5A, 5B:
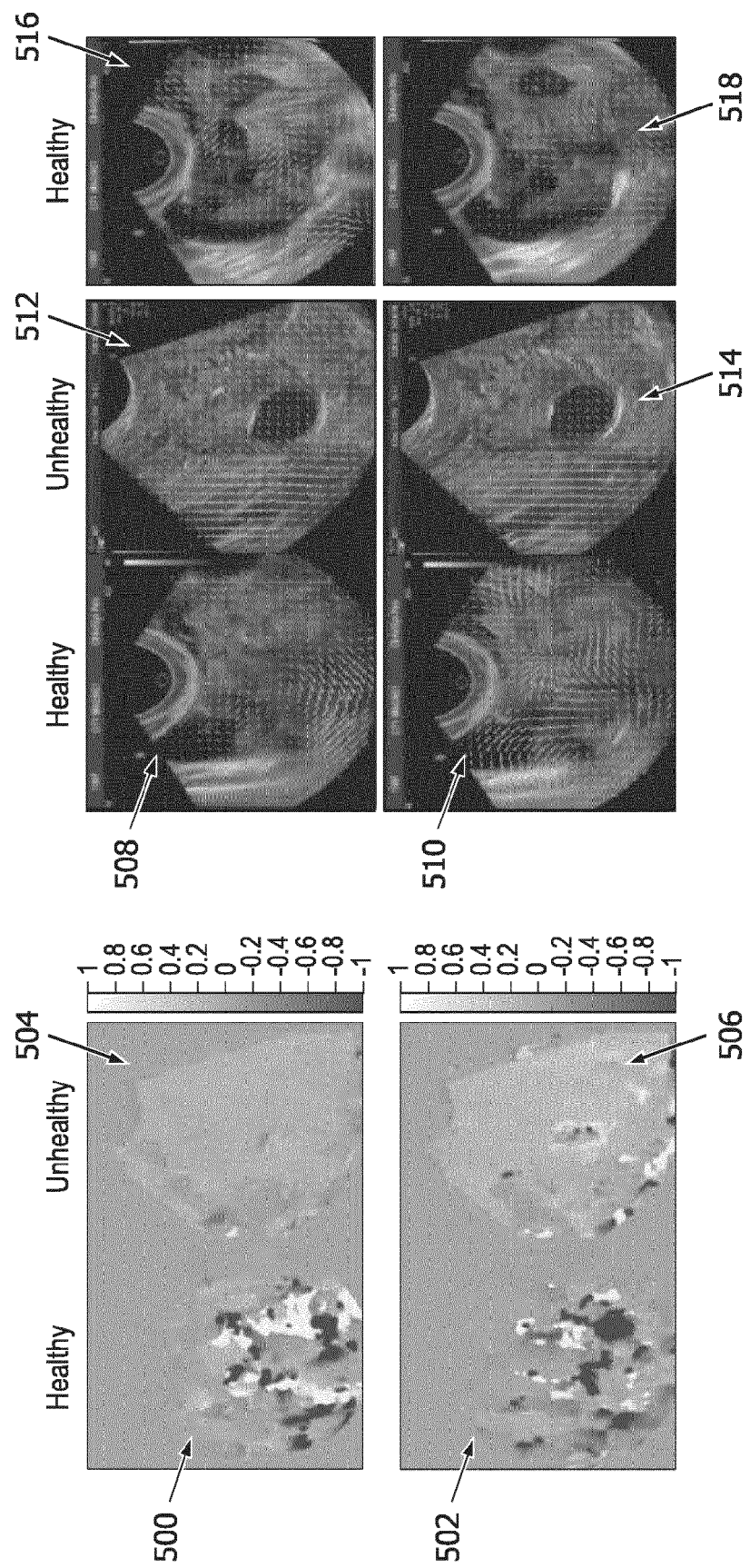
FIG. 5A shows example displacement maps in accordance with principles of the present disclosure.
FIG. 5B shows example velocity maps in accordance with principles of the present disclosure.

FIG. 5A shows example displacement maps in accordance with principles of the present disclosure. In some examples, displacement maps may be generated from values of displacement fields generated by normalizing the flow fields (e.g., flow fields 404) output by a motion analysis AI model, such as motion analysis AI model 308. The displacement maps 500 and 502 were generated based on data acquired from ovarian mobility exams of a healthy subject, and displacement maps 504 and 506 were generated based on data acquired from a subject suffering from endometriosis (e.g., unhealthy subject). In the displacement maps 500, 502 of the healthy subject, the pattern of the flow fields is more heterogeneous than in the displacement maps 504, 506 of the unhealthy subject, suggesting that the displacement is very chaotic. In contrast, for the unhealthy subject where the pelvic tissue is moving altogether in the same direction with high correlation as shown by the large areas of uniform shading of the displacement maps 505, 506, suggesting the obliteration seems severe. It is clear that the frame-to-frame displacement is much more chaotic in the healthy subject.

FIG. 5B shows example velocity maps in accordance with principles of the present disclosure. Velocity maps may provide vectors illustrated as quiver arrows overlaid on an image frame where the vectors indicate the direction and magnitude of motion of the pixels of the image frame. The velocity maps may be generated based values of velocity vectors based on the tracking of motion of landmarks in a sequence of image frames, for example, based on flow fields output by a motion analysis AI model, such as motion analysis AI model 308. The velocity maps 508, 510, 516 and 518 were generated based on data acquired from ovarian mobility exams of healthy subjects, and velocity maps 512 and 514 were generated based on data acquired from a subject suffering from endometriosis (e.g., unhealthy subject) In some applications, healthy cases may be associated with chaotic or random distribution of velocity vectors (e.g., anisotropic), while a more isotropic distribution is associated with the unhealthy cases. In some applications, velocity mapping may help users understand the degree of tissue obliteration. For example, in velocity maps 512 and 514, the quiver arrows are all moving to almost the same direction in the unhealthy case (up and down). In contrast, there is a more chaotic movement for the healthy subjects, where the velocity vectors point in a variety of different directions in velocity maps 508, 510, 516, and 518.

The displacement and velocity data used to generate the displacement and velocity maps shown in FIGS. 5A and 5B, respectively, may be used to generate a quantitative metric for organ mobility referred to as displacement/velocity isotropy. The displacement/velocity isotropy is calculated as the ratio of the magnitude of spatially averaged displacement/velocity vectors and the magnitude of displacement/velocity vectors (e.g., the average of the data from the displacement maps shown in FIG. 5A and the average magnitude of the data from the velocity maps shown in FIG. 5B). The placement/velocity isotropy is a dimensionless parameter and may be used to quantify the displacement/velocity pattern of the moving tissue.

Figure 6:
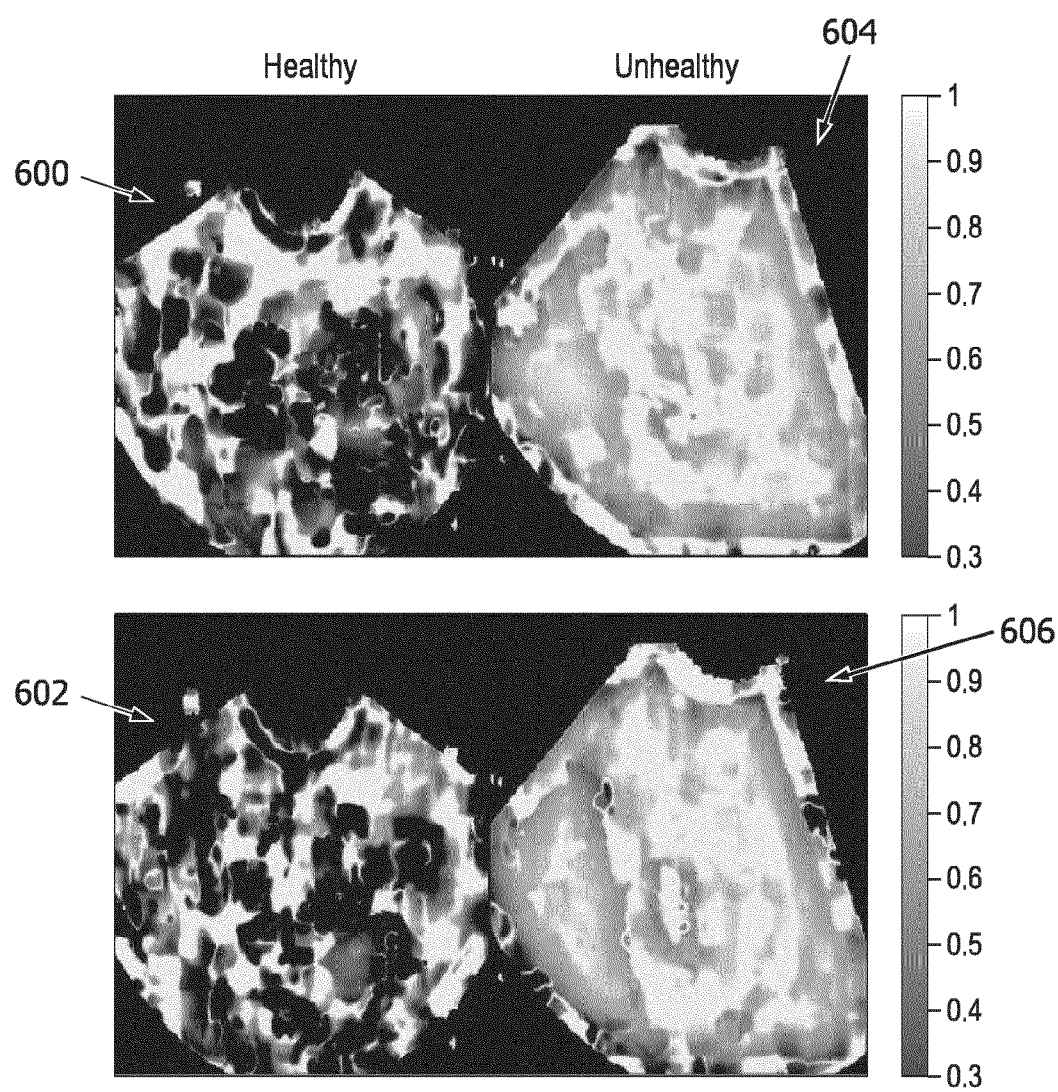
FIG. 6 shows example mobility maps in accordance with principles of the present disclosure.

FIG. 6 shows example mobility maps in accordance with principles of the present disclosure. The mobility maps 600 and 602 were generated from data acquired from a healthy subject during a mobility exam and mobility maps 604 and 606 were generated from data acquired from a subject suffering from endometriosis (e.g., unhealthy subject). The mobility maps 600, 602, 604, and 606 are a graphical representation of the displacement/velocity isotropy, which is generated from the data used to generate the displacement and velocity maps, such as the displacement and velocity maps shown in FIGS. 5A and 5B. The number of displacement/velocity isotropy values may be equal to a number of pixels in an image frame from a sequence of image frames that were analyzed in some examples.

In the healthy subject, the tissue motions are very chaotic in multiple directions. As seen in the mobility maps 600, 602, the spatially averaged displacement/velocity vectors are cancelled out, resulting in very low isotropy/high anisotropy (e.g., values close to zero). In some applications, anisotropic movement may be associated with and/or referred to as "mobility." In the unhealthy subject, the tissue motions are much more uniform in almost the same direction. In mobility maps 604, 606, the spatially averaged displacement/velocity vectors are not cancelled out at all, resulting in very high isotropy (e.g., values close to one).

While the displacement/velocity isotropy is a quantitative measure of mobility, mobility maps, such as those shown in FIG. 6 may be difficult for users, particularly novice users, to interpret. Accordingly, in some applications, a more user-friendly depiction of the mobility may be provided to the user.

Figure 7:
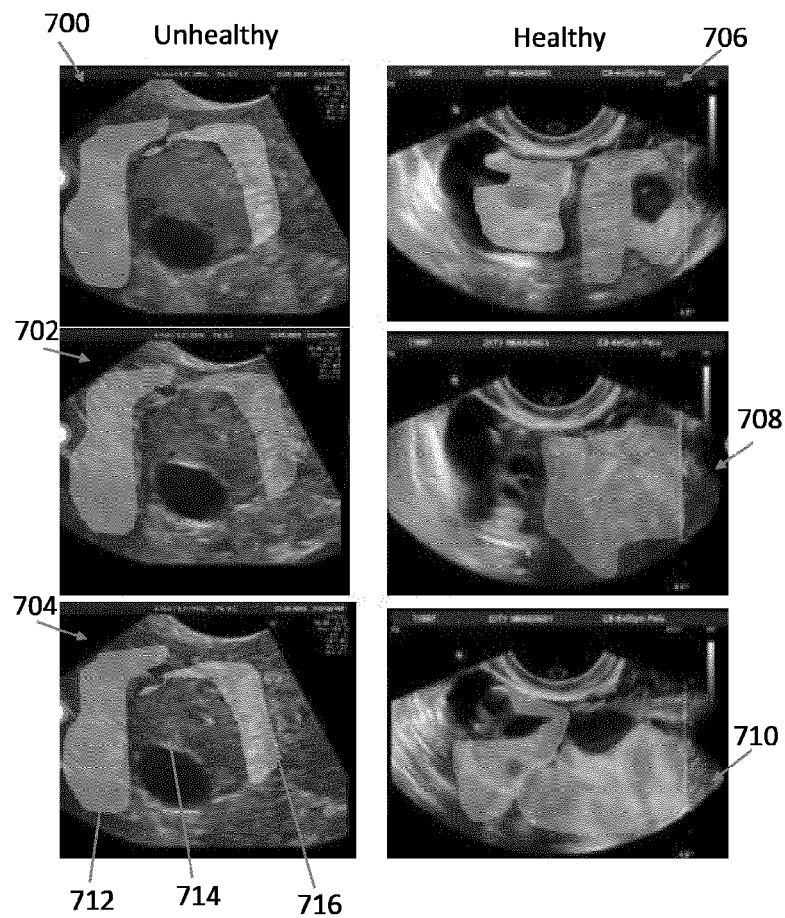
FIG. 7 shows examples of mobility masks according to principles of the present disclosure.

FIG. 7 shows examples of mobility masks according to principles of the present disclosure. The mobility masks 700, 702, and 704 were generated from data acquired from a subject suffering from endometriosis (e.g., unhealthy subject) during a mobility exam and mobility masks 706, 708, and 710 were generated from data acquired from a healthy subject. The mobility masks shown in FIG. 7 may be generated by segmenting corresponding mobility maps, such as those shown in FIG. 6. Regions having equal and/or similar displacement/velocity isotropy values may be grouped into different regions, such as regions 712, 714, and 716 indicated in mobility mask 704. In some examples, the regions 712, 714, 716 may be based on threshold values and/or ranges of values for the displacement/velocity isotropy values. In some examples, regions having different displacement/velocity isotropy values or ranges thereof, may be displayed with different colors, patterns, and/or intensities. In some examples, such as the one shown in FIG. 7, the mobility masks may be overlaid onto one or more image frames from a sequence of image frames (e.g., sequence of image frames 300). In some examples, a mobility mask may be provided on a display, such as display 238, side-by-side with a corresponding mobility map.

The information displayed on the mobility mask may provide easier to interpret information (in comparison to the mobility map) relating to a degree of landmark displacement in the field of view along with the isotropy/anisotropy information related to the distribution of the velocity vectors. For example, freely moving ovaries, as shown in mobility masks 706, 708, and 710 display low degree of obliteration of the pelvic landmarks. In the presence of tissue obliteration and endometriosis, such as in mobility masks 700, 702, and 704, the ovaries may appear "fixed" and some or all of the landmarks may move all together as a block, displaying a very high displacement isotropy of the velocity vectors.

In some applications, generation of a visual feedback to the user showing the degree of obliteration, such as with a mobility mask as shown in FIG. 7, may help the user visualize the onset of medical conditions associated with organ mobility, such as endometriosis, at an early stage.

As noted previously, the mobility is based on the amount of "free moving" tissue versus the amount of "fixed" tissue. For example, the mobility index may be based on a percentage of pixels having displacement/velocity isotropy values equal to or below a threshold value versus a total number of pixels. For example, the unhealthy subject on the left-side of FIG. 7 may have a mobility index of 15% whereas the healthy subject on the right-side of FIG. 7 may have a mobility index of 75%. In some examples, the mobility index may be displayed with the mobility mask and/or mobility map. In some examples, the mobility index may be displayed with an image frame without the mobility mask and/or mobility map displayed.

Optionally, the flow fields (e.g., flow fields 404) and/or the data from the displacement and velocity maps generated from the flow fields (e.g., the displacement and velocity maps shown in FIGS. 5A and 5B) may be analyzed by a cluster analysis AI model, such as cluster analysis AI model 314. FIG. 8 is an example cluster map of pelvic organs according to principles of the present disclosure. The cluster map 800 clusters pelvic organs (e.g., landmarks) by displacement. The cluster map 800 may provide insight into which organs are fused and/or impacting the mobility of other organs.

Figure 9:
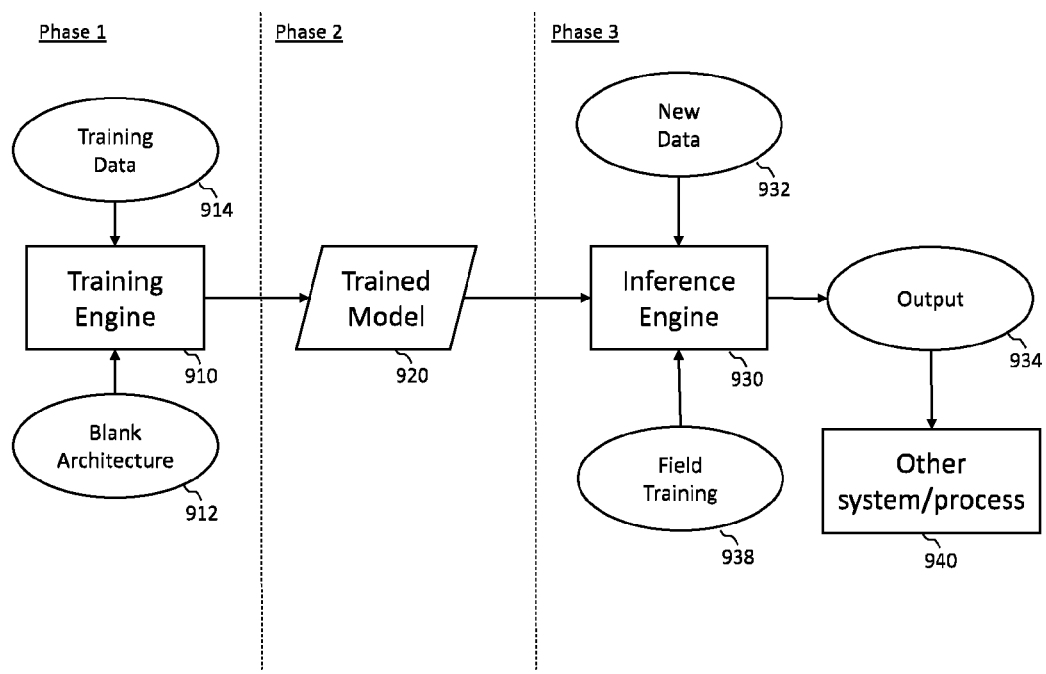
FIG. 9 is a block diagram of a process for training and deployment of a neural network in accordance with the principles of the present disclosure.

FIG. 9 shows a block diagram of a process for training and deployment of a neural network in accordance with the principles of the present disclosure. The process shown in FIG. 9 may be used to train an AI model implemented by a medical imaging system, such as the AI models shown in FIG. 3. The left hand side of FIG. 9, phase 1, illustrates the training of an AI model. To train the AI model, training sets which include multiple instances of input arrays and output classifications may be presented to the training algorithm(s) of the AI model(s) (e.g., AlexNet training algorithm, as described by Krizhevsky, A., Sutskever, I. and Hinton, G. E. "ImageNet Classification with Deep Convolutional Neural Networks," NIPS 2012 or its descendants). Training may involve the selection of a starting architecture 912 and the preparation of training data 914. The starting architecture 912 may be a blank architecture (e.g., an architecture with defined layers and arrangement of nodes but without any previously trained weights) or a partially trained model, such as the inception networks, which may then be further tailored for classification of ultrasound images. The starting architecture 912 (e.g., blank weights) and training data 914 are provided to a training engine 910 (e.g., ADAM optimizer) for training the model. Upon sufficient number of iterations (e.g., when the model performs consistently within an acceptable error), the model 920 is said to be trained and ready for deployment, which is illustrated in the middle of FIG. 9, phase 2. The right hand side of FIG. 9, or phase 3, the trained model 920 is applied (via inference engine 930) for analysis of new data 932, which is data that has not been presented to the model during the initial training (in phase 1). For example, the new data 932 may include unknown images such as live ultrasound images acquired during a scan of a patient (e.g., pelvic images during a mobility exam). The trained model 920 implemented via engine 930 is used to classify the unknown images in accordance with the training of the model 920 to provide an output 934 (e.g., generating bounding boxes, flow fields, cluster map.). The output 934 may then be used by the system for subsequent processes 940 (e.g., generating displacement and/or velocity maps, generating mobility maps and/or masks, generating an OMI).

In the embodiments where the trained model 920 is used to implement a neural network executed by a processor, such as image processor 236, the starting architecture may be that of a convolutional neural network, or a deep convolutional neural network, which may be trained to detect landmarks, analyze movement, and/or perform cluster analysis of landmarks. The training data 914 may include multiple (hundreds, often thousands or even more) annotated/labeled images, also referred to as training images. It will be understood that the training image need not include a full image produced by an imagining system (e.g., representative of the full field of view of an ultrasound probe or entire MRI volume) but may include patches or portions of images, for example, those portions that include organs of interest.

In various embodiments, the trained AI model may be implemented, at least in part, in a computer-readable medium comprising executable instructions executed by a processor, e.g., image processor 236.

In some examples, to obtain ground truth for detecting landmarks for training a landmark detection AI model, such as landmark detection AI model 304, trained sonographers may annotate B-mode images of sequences of B-mode images by placing bounding boxes around each organ (e.g., landmark) present in the field of view (e.g., visible in the image frame). In some applications, such as for endometriosis detection, this labeling procedure may be done on each TVUS B-mode frame acquired during a push-pull mobility assessment procedure. In some examples, the organs labeled by the bounding boxes of the set of training images may be leveraged to also generate a ground truth optical flow mask to train a movement analysis AI model, such as movement analysis AI model 308.

Figure 10:
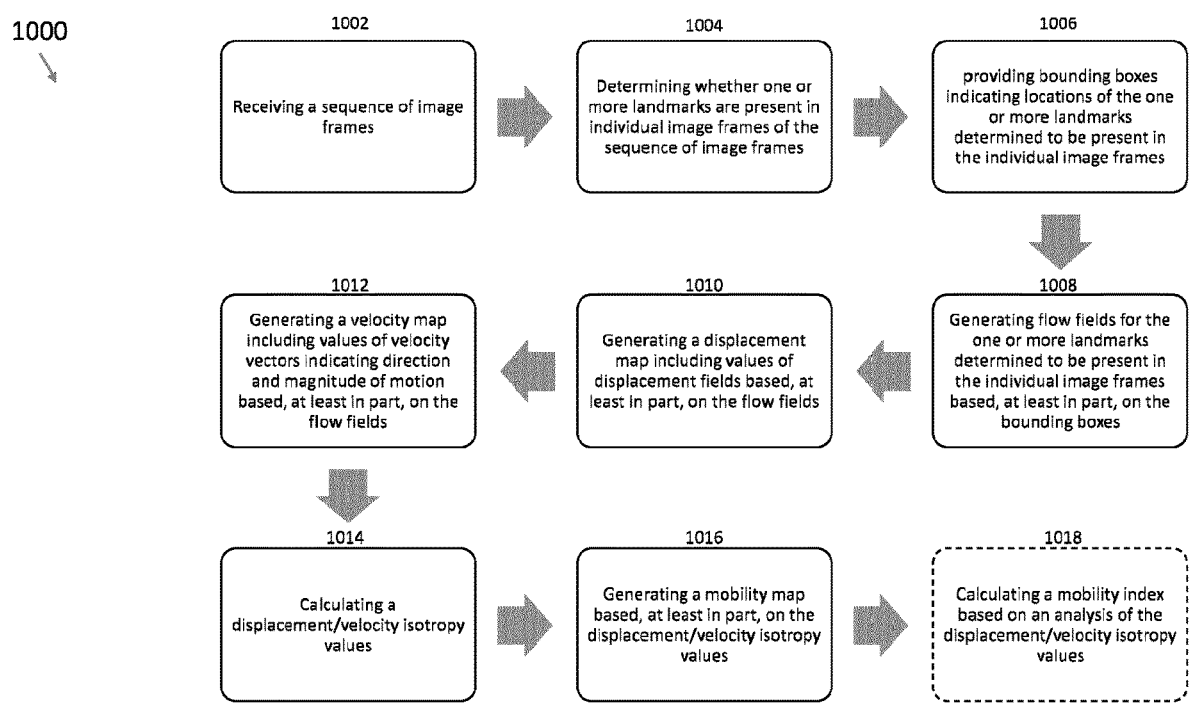
FIG. 10 is a flow chart of a method in accordance with principles of the present disclosure.

FIG. 10 is a flow chart of a method according to principles of the present disclosure. In some examples, the method 1000 may be performed in whole or in part by an ultrasound imaging system, such as system 200 shown in FIG. 2. In some examples, the method 1000 may be performed in whole or in part by at least one processor of the ultrasound imaging system, such as image processor 236. The method 1000 may provide quantification of landmark mobility. Landmarks may include organs, blood vessels, other physiological features, and/or implanted devices.

As indicated at block 1002, the at least one processor may receive a sequence of image frames. In some examples, the image frames may be B-mode image frames. In some examples, the sequence may be a temporal sequence. As indicated at blocks 1004 and 1006, the at least one processor may determine whether one or more landmarks are present in individual image frames of the sequence of image frames and provide bounding boxes indicating locations of the one or more landmarks determined to be present in the individual image frames. In some examples, the determining whether the one or more landmarks are present and providing the bounding boxes are performed by an AI model implemented by the one or more processors, such as landmark detection AI model 304.

The at least one processor may generate flow fields for the one or more landmarks determined to be present in the individual image frames based, at least in part, on the bounding boxes or alternatively on the whole frame, as indicated by block 1008. In some examples, generating the flow fields is performed by an AI model implemented by the at least one processor, such as movement analysis AI model 308. In some examples, the AI model includes a FlowNet network, such as FlowNet network 400.

The at least one processor may generating a displacement map including values of displacement fields and a velocity map including values of velocity vectors indicating direction and magnitude of motion based, at least in part, on the flow fields as indicated by blocks 1010 and 1012.

As indicated at block 1014, the at least one processor may calculate a displacement/velocity isotropy values. In some examples, the values may be calculated by taking a ratio of a magnitude of spatially averaged displacement fields divided by the magnitude of displacement fields/velocity vectors.

The at least one processor may generate a mobility map based, at least in part, on the displacement/velocity isotropy values as indicated at block 1016.

Optionally, in some examples, as indicated at block 1018, the at least one processor may calculate a mobility index based on an analysis of the displacement/velocity isotropy values.

Optionally, in some examples, the at least one processor may segment the mobility map based, at least in part, on the displacement/velocity isotropy values and generate a mobility mask including one or more regions based, at least in part, on segmentation of the mobility map. The mobility mask may be displayed with the mobility map and/or overlaid on an image frame of the image sequence of image frames.

Optionally, the at least one processor may cluster the one or more landmarks present in individual image frames of the sequence of image frames based on at least one of relative movement or absolute movement of the one or more landmarks. In some examples, clustering is performed by an AI model implemented by the at least one processor, such as cluster analysis AI model 314. In some examples, the AI model includes a G-means clustering algorithm.

Optionally, in some examples, the at least one processor may receive probe movement data for an ultrasound probe (e.g., ultrasound probe 212) from an inertial measurement unit (e.g., IMU 270) and exclude individual images of the image sequence from the image sequence associated with at least one of abrupt motion of the ultrasound probe or rotational motion of the ultrasound probe.

Figure 11:
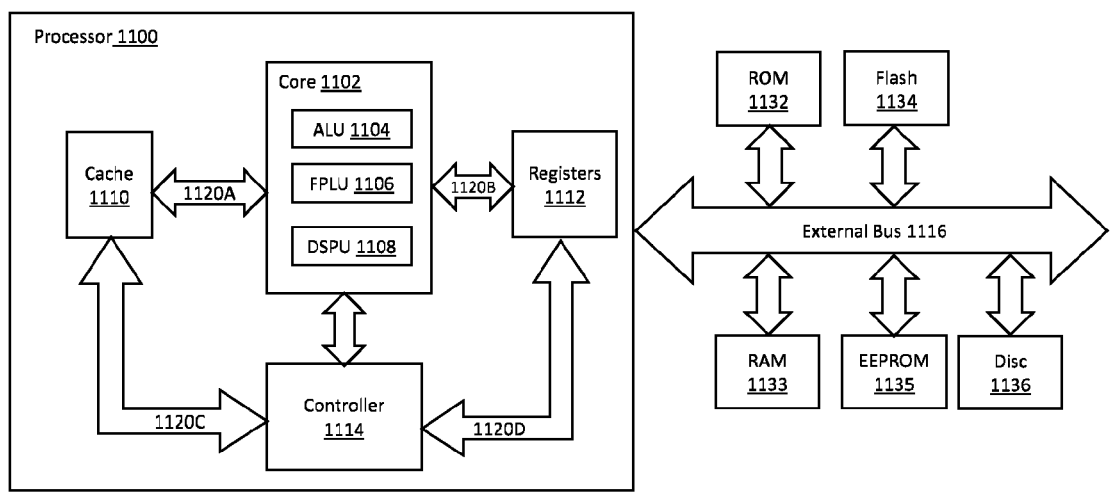
FIG. 11 is a block diagram illustrating an example processor in accordance with principles of the present disclosure.

FIG. 11 is a block diagram illustrating an example processor 1100 according to principles of the present disclosure. Processor 1100 may be used to implement one or more processors and/or controllers described herein, for example, image processor 236 shown in FIG. 2 and/or any other processor or controller shown in FIG. 2. Processor 1100 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 1100 may include one or more cores 1102. The core 1102 may include one or more arithmetic logic units (ALU) 1104. In some embodiments, the core 1102 may include a floating point logic unit (FPLU) 1106 and/or a digital signal processing unit (DSPU) 1108 in addition to or instead of the ALU 1104.

The processor 1100 may include one or more registers 1112 communicatively coupled to the core 1102. The registers 1112 may be implemented using dedicated logic gate circuits (e.g., flip-flops) and/or any memory technology. In some embodiments the registers 1112 may be implemented using static memory. The register may provide data, instructions and addresses to the core 1102.

In some embodiments, processor 1100 may include one or more levels of cache memory 1110 communicatively coupled to the core 1102. The cache memory 1110 may provide computer-readable instructions to the core 1102 for execution. The cache memory 1110 may provide data for processing by the core 1102. In some embodiments, the computer-readable instructions may have been provided to the cache memory 1110 by a local memory, for example, local memory attached to the external bus 1116. The cache memory 1110 may be implemented with any suitable cache memory type, for example, metal-oxide semiconductor (MOS) memory such as static random access memory (SRAM), dynamic random access memory (DRAM), and/or any other suitable memory technology.

The processor 1100 may include a controller 1114, which may control input to the processor 1100 from other processors and/or components included in a system (e.g., control panel 252 and scan converter 230 shown in FIG. 2) and/or outputs from the processor 1100 to other processors and/or components included in the system (e.g., display 238 and volume renderer 234 shown in FIG. 2). Controller 1114 may control the data paths in the ALU 1104, FPLU 1106 and/or DSPU 1108. Controller 1114 may be implemented as one or more state machines, data paths and/or dedicated control logic. The gates of controller 1114 may be implemented as standalone gates, FPGA, ASIC or any other suitable technology.

The registers 1112 and the cache memory 1110 may communicate with controller 1114 and core 1102 via internal connections 1120A, 1120B, 1120C and 1120D. Internal connections may implemented as a bus, multiplexor, crossbar switch, and/or any other suitable connection technology.

Inputs and outputs for the processor 1100 may be provided via a bus 1116, which may include one or more conductive lines. The bus 1116 may be communicatively coupled to one or more components of processor 1100, for example the controller 1114, cache memory 1110, and/or register 1112. The bus 1116 may be coupled to one or more components of the system, such as display 238 and control panel 252 mentioned previously.

The bus 1116 may be coupled to one or more external memories. The external memories may include Read Only Memory (ROM) 1132. ROM 1132 may be a masked ROM, Electronically Programmable Read Only Memory (EPROM) or any other suitable technology. The external memory may include Random Access Memory (RAM) 1133. RAM 1133 may be a static RAM, battery backed up static RAM, Dynamic RAM (DRAM) or any other suitable technology. The external memory may include Electrically Erasable Programmable Read Only Memory (EEPROM) 1135. The external memory may include Flash memory 1134. The external memory may include a magnetic storage device such as disc 1136. In some embodiments, the external memories may be included in a system, such as ultrasound imaging system 200 shown in FIG. 2, for example local memory 242.

The systems, methods, and apparatuses disclosed herein may provide a quantitative and operator independent technique based on deep learning to characterize organ mobility. Intelligent assessment of the organ mobility may be made by examining the motion of the organ with respect to adjacent organs. During a mobility exam by a sonographer, the systems, methods, and apparatuses may track the global displacement and calculate the displacement/velocity isotropy for pelvic landmarks in B-mode ultrasound. A metric called an mobility index and/or obliteration index may be used to cluster pelvic landmarks that move together (e.g., ovaries and uterus move as a single block in presence of deep infiltrating pelvic endometriosis) and generate a mobility mask. The quantification and visualization of organ mobility may aid physicians in making a more confident diagnosis of certain medical conditions, such as endometriosis.

Although the examples described herein discuss processing of ultrasound image data, it is understood that the principles of the present disclosure are not limited to ultrasound and may be applied to image data from other modalities such as magnetic resonance imaging and computed tomography.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "C #", "Java", "Python", and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system configured to provide quantification of landmark mobility, the system comprising:
    a non-transitory computer readable medium encoded with instructions and configured to store a temporal sequence of image frames; and
    at least one processor in communication with the non-transitory computer readable medium and configured to execute the instructions, wherein when executed, the instructions cause the at least one processor to:
        determine whether one or more landmarks are present in individual image frames of the sequence of image frames;
        output bounding boxes indicating locations of the one or more landmarks determined to be present in the individual image frames;
        output flow fields for the one or more landmarks determined to be present in the individual image frames based, at least in part, on the bounding boxes;
        generate values of displacement fields based, at least in part, on the flow fields;
        generate values of velocity vectors indicating direction and magnitude of motion based, at least in part, on the flow fields;
        calculate DVIS (displacement-velocity isotropy values) by taking a ratio of a magnitude of spatially averaged displacement fields divided by the velocity vectors; and
        generate at least one of a mobility map or a mobility index based, at least in part, on the DVIS.

2. The system of claim 1, wherein the mobility index is based on a percentage of values equal to or below a threshold value.

3. The system of claim 1, wherein the DVIS are indicative of a clinical condition or a severity of the clinical condition.

4. The system of claim 3, wherein the clinical condition comprises endometriosis.

5. The system of claim 1, wherein the instructions further cause the at least one processor to:
    segment the mobility map based, at least in part, on the DVIS; and
    generate a mobility mask including one or more regions based, at least in part, on segmentation of the mobility map.

6. The system of claim 5, wherein the one or more regions have at least one of different values or ranges of values of the DVIS.

7. The system of claim 5, wherein the instructions further cause the at least one processor to generate display data for overlaying the mobility mask on an image frame of the sequence of image frames.

8. The system of claim 1, wherein the instructions further cause the at least one processor to cluster the one or more landmarks present in individual image frames of the sequence of image frames based on at least one of relative movement or absolute movement of the one or more landmarks.

9. The system of claim 1, further comprising:
    an ultrasound probe including an inertial measurement unit configured to measure movement of the ultrasound probe and output probe movement data,
    wherein the instructions further cause the at least one processor to exclude individual image frames from the sequence of image frames from analysis based, at least in part, on the probe movement data.

10. The system of claim 9, wherein the individual image frames excluded are associated with at least one of abrupt motion of the ultrasound probe or rotational motion of the ultrasound probe based on the probe movement data.

11. The system of claim 9, further comprising a user interface,
    wherein the instructions further cause the at least one processor to provide feedback on properly executed probe motion via the user interface.

12. The system of claim 1, wherein the instructions further cause the at least one processor to generate at least one of a displacement map based on the values of the displacement fields or a velocity map based on the values of the velocity vectors.

13. A method for providing quantification of landmark mobility, the method comprising:
    receiving a sequence of image frames;
    determining whether one or more landmarks are present in individual image frames of the sequence of image frames;
    providing bounding boxes indicating locations of the one or more landmarks determined to be present in the individual image frames;
    generating flow fields for the one or more landmarks determined to be present in the individual image frames based, at least in part, on the bounding boxes or entire frames of the sequence of image frames;
    generating values of displacement fields based, at least in part, on the flow fields;
    generating values of velocity vectors indicating direction and magnitude of motion based, at least in part, on the flow fields;
    calculating DVIS (displacement-velocity isotropy values) by taking a ratio of a magnitude of spatially averaged displacement fields divided by the velocity vectors; and
    generating at least one of a mobility map or a mobility index based, at least in part, on the DVIS.

14. The method of claim 13, wherein the determining whether the one or more landmarks are present and providing the bounding boxes are performed by a first artificial intelligence (AI) model and wherein generating the flow fields is performed by a second artificial intelligence (AI) model.

15. A non-transitory computer-readable medium comprising computer readable medium the computer readable medium having computer readable code embodied therein, characterized by the computer readable code being configured such that, on execution by a suitable computer or processor, the computer or processor is caused to perform the method as claimed in claim 13.

* * * * *